United States Patent [19]

Inoue et al.

[11] Patent Number: 4,983,759
[45] Date of Patent: Jan. 8, 1991

[54] PROCESS FOR THE PRODUCTION OF 3,5,6-TRIHYDROXYHEXANOIC ACID DERIVATIVE

[75] Inventors: Kenji Inoue; Satomi Takahashi; Keiichi Yonetsu; Noboru Ueyama, all of Hyogo, Japan

[73] Assignee: Kanegafuchi Chemical Industry Co., Ltd., Osaka, Japan

[21] Appl. No.: 452,470

[22] Filed: Dec. 20, 1989

[30] Foreign Application Priority Data

Dec. 21, 1988 [JP] Japan ................................ 63-323935

[51] Int. Cl.$^5$ ...................... C07C 69/66; C07D 317/18
[52] U.S. Cl. ........................................ 500/174; 560/185; 560/186; 560/112; 549/454; 549/342; 549/375; 556/437; 552/105; 558/52
[58] Field of Search ............... 560/174, 185, 186, 112; 549/454, 342, 375; 556/437; 552/105; 558/52

[56] References Cited

PUBLICATIONS

Protective Groups in Organic Chemistry, ed. J.F.W. McOvie, Plenam Press, New York, N.Y., 1973, pp. 95-143.

Primary Examiner—Nicky Chan
Attorney, Agent, or Firm—Wegner, Cantor, Mueller & Player

[57] ABSTRACT

A compound of a 3,5,6-trihydroxyhexanoic acid derivative of the formula:

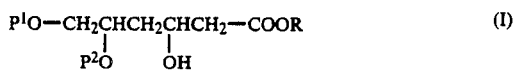

(I)

wherein $P^1$ and $P^2$ are independently hydrogen atoms or hydroxy-protecting groups, or together form a ring, and R is an alkyl group is effectively prepared by a process comprising steps of:
reacting a butyronitrile derivative of the formula:

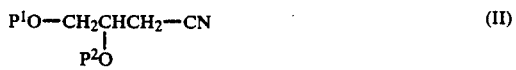

(II)

wherein $P^1$ and $P^2$ are the same as defined above with an α-haloacetate of the formula:

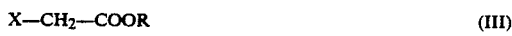

(III)

wherein X is a halogen atom, and R is the same as defined above in the presence of a metallic catalyst selected from the group consisting zinc and zinc-copper to form a keto acid derivative of the formula:

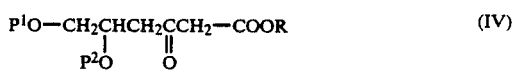

(IV)

wherein $P^1$, $P^2$ and R are the same as defined above, and
then reducing the obtained keto-acid derivative of the formula (IV).

8 Claims, No Drawings

PROCESS FOR THE PRODUCTION OF 3,5,6-TRIHYDROXYHEXANOIC ACID DERIVATIVE

BACKGROUND OF THE INVENTION

1. Field of the Invention

The present invention relates to a process for the production of 3,5,6-trihydroxyhexanoic acid derivatives.

The 3,5,6-trihydroxyhexanoic acid derivatives are useful as intermediates in the synthesis of a series of HMG-CoA (Hydroxy methyl glutaryl-CoA) reductase inhibitors which are attractive as anti-hyperlipemia agents.

2. Description of the Related Art

To prepare the 3,5,6-trihydroxyhexanoic acid derivatives, the following processes are known:

(A) A process using L-malic acid as a starting material (cf. Japanese Patent Kokai Publication No. 22056/1988):

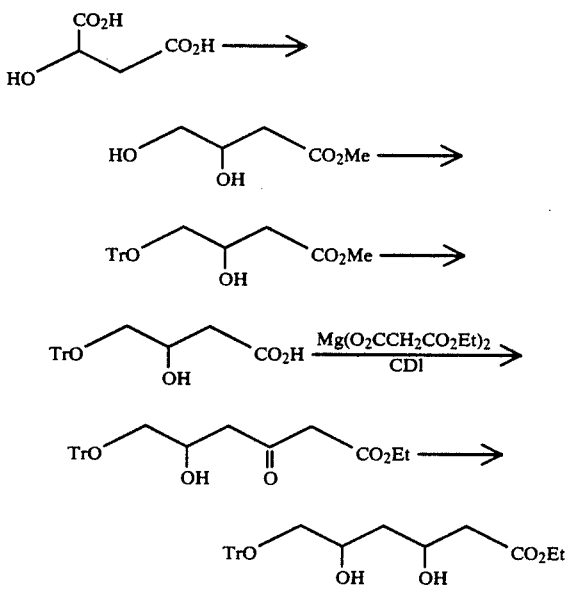

(B) A process using 1,3,5-trihydroxybenzene (Phloroglucinol) as a starting material (cf. Tetrahedron Letters, 23, 2435 (1984) and U.S. Pat. No. 4,571,428):

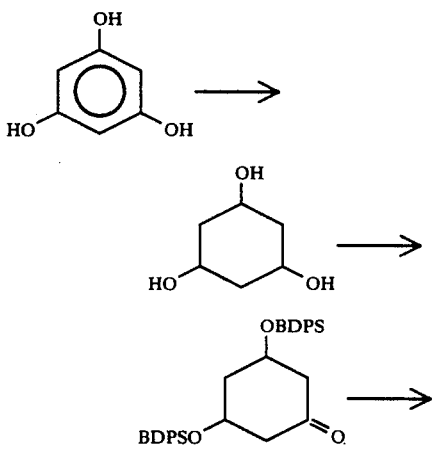

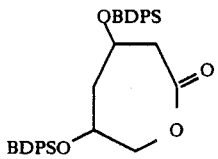

(C) A process using an allyl alcohol derivative as a starting material (cf. Tetrahedron Letters, 25, 3391 (1984)):

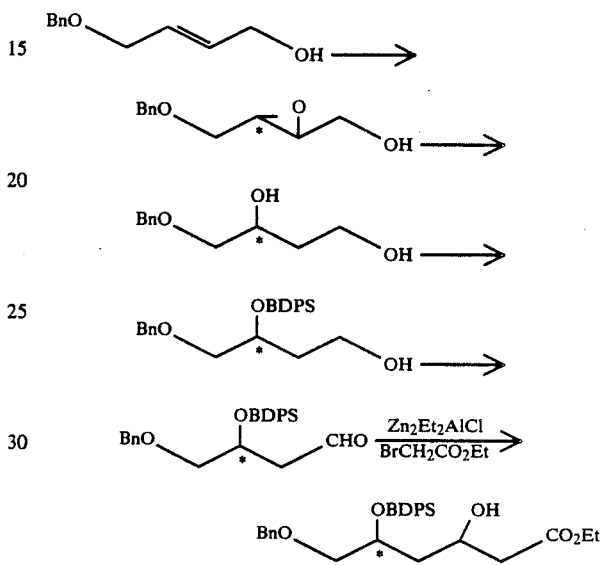

Among the above conventional processes, the process (A) has an advantage that the product can be obtained in an optically active form. However, the process (A) requires a multistage reaction and relatively expensive reagents such as carbonyl diimidazole.

In the process (B), although the reaction time is not long, the product is obtained in the form of racemate. The useful compound as HMG-CoARI intermediate should have a (3R, 5S) configuration.

The third process (C) gives the optically active product. However, there is no optical selectivity in the reaction of an aldehyde and ethyl bromoacetate. Therefore, this process is not industrially attractive.

SUMMARY OF THE INVENTION

An object of the present invention is to provide a novel process for the production of a 3,5,6-trihydroxyhexanoic acid derivative, which is effective, economical and industrially attractive.

Accordingly, the present invention provides a process for the production of a 3,5,6-trihydroxyhexanoic acid derivative of the formula:

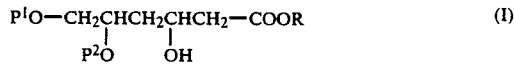

wherein $P^1$ and $P^2$ are independently hydrogen atoms or hydroxyl-protecting groups, or together form a ring, and R is an alkyl group, which comprises steps of: reacting a butyronitrile derivative of the formula:

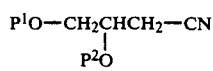 (II)

wherein $P^1$ and $P^2$ are the same as defined above with an α-haloacetate of the formula:

$$X-CH_2-COOR \quad (III)$$

wherein X is a halogen atom, and R is the same as defined above in the presence of a metallic catalyst selected from the group consisting zinc and zinc-copper to form a keto acid derivative of the formula:

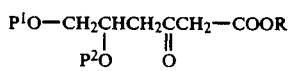 (IV)

wherein $P^1$, $P^2$ and R are the same as defined above, and then reducing the obtained keto acid derivative of the formula (IV).

DETAILED DESCRIPTION OF THE INVENTION

Herein, the alkyl or alkoxy group intends to mean those having 1 to 10 carbon atoms, preferably 1 to 4 carbon atoms such as methyl, ethyl, n-propyl, iso-propyl, n-butyl, iso-butyl and tert.-butyl.

In the process of the present invention, as the butyronitrile derivative (II), 3,4-dihydroxybutyronitrile is preferably used. 3,4-Dihydroxybutyronitrile can be prepared by cyanating 3-chloro-1,2-propanediol.

As the butyronitrile derivative (II), hydroxy group-protected 3,4-dihydroxybutyronitrile may be used. Examples of the protecting groups are a triphenylmethyl group, an acetonide group, a benzoyl group, a substituted benzoyl group, a p-toluenesulfonyl group, a methanesulfonyl group, an acetyl group, a substituted silyl group and the like.

When $P^1$ is a triphenylmethyl group, the crystallinity of the butyronitrile derivative (II) is increased so that it is easily isolated.

The butyronitrile derivative (II) wherein $P^1$ is a triphenylmethyl group and $P^2$ is a hydrogen atom can be easily prepared by treating 3,4-dihydroxybutyronitrile with triphenylmethyl chloride, for example, in a mixed solvent of methylene chloride and pyridine. The crude product can be easily isolated and purified by conventional methods, for example, recrystallization from a suitable solvent such as hexane/ethyl acetate.

The butyronitrile derivative (II) wherein $P^1$ and $P^2$ are both acetonide groups can be easily prepared by reacting 3,4-dihydroxybutyronitrile with 2,2-dimethoxypropane and/or acetone.

The butyronitrile derivative (II) wherein $P^1$ is a benzoyl group and $P^2$ is a hydrogen atom can be easily prepared by reacting 3,4-dihydroxybutyronitrile with benzoyl chloride in a solvent such as pyridine.

In addition, an optically active (3S)-butyronitrile derivative can be used as the butyronitrile derivative of the formula (II). In this case, an optically active (5S)-trihydroxyhexanoic acid derivative is obtained as the 3,5,6-trihydroxyhexanoic acid of the formula (I).

Preferred examples of the butyronitrile derivative (II) are a compound of the formula:

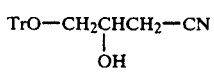 (IIa)

wherein Tr is a triphenylmethyl group, a compound of the formula:

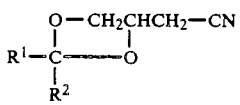 (IIb)

wherein $R^1$ and $R^2$ are independently hydrogen atoms, alkyl groups or aryl groups, or together form a 5- or 6-membered ring together with the carbon atom to which they are bonded, a compound of the formula:

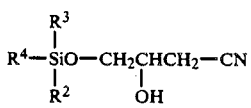 (IIc)

wherein $R^3$ and $R^4$ are independently alkyl or aryl groups, and a compound of the formula:

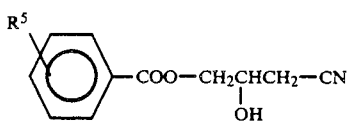 (IId)

wherein $R^5$ is a hydrogen atom, an alkyl, alkoxy group or a halogen atom.

Among the α-haloacetate (III), α-bromoacetates such as ethyl α-bromoacetate, methyl α-bromoacetate, tert.butyl α-bromoacetate and the like are preferred.

The reaction between the butyronitrile derivative (II) and the α-haloacetate (III) is carried out in a suitable solvent in the presence of a metallic catalyst.

As the metallic catalyst, zinc which is activated with hydrochloric acid and the like and zinc-copper are preferred since they accelerate the reaction and give the product in a high yield. Examples of the solvent are tetrahydrofuran, dimethylformamide, dimethylsulfoxide, benzene, toluene, hexane, cyclohexane and mixtures thereof.

This reaction may be carried out by adding, for example, ethyl α-bromoacetate to a solution of the butyronitrile derivative (II) in tetrahydrofuran in the presence of activated zinc at a temperature from room temperature to 80° C., preferably from 50° to 70° C. In this case, ethyl α-bromoacetate is preferably added dropwise to suppress self-condensation of the acetate. However, the reaction manner is not limited to the above manner.

The primary reaction product prepared by the above reaction is an enamine or a Schiff's base of the formula:

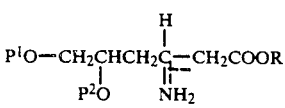 (VII)

wherein $P^1$, $P^2$ and R are the same as defined above, and the keto acid derivative (IV) is prepared by hydrolyzing the enamine or the Schiff's base.

The keto acid derivative (IV) can be easily reduced with a reducing agent which reduces a ketone to an alcohol or by catalytic hydrogenation. Examples of the reducing agent are sodium borohydride, zinc borohydride, lithium borohydride, diisobutylaluminum hydride, sodium bis(2-methoxyethoxy)aluminum hydride and the like. In the reduction of the keto acid derivative (IV), the obtained compound (I) is a mixture of the syn-form and the anti-form isomers. When a hydride type reducing agent is used, the syn-form stereoisomer of the compound (I), which is useful as the intermediate for the synthesis of the HMG-CoA reductase inhibitor, is favorably produced. Stereospecificity of the reaction varies with a combination of the keto acid derivative (IV) and the reducing manner. When a combination of sodium borohydride and trialkylborane, or diisobutylaluminum hydride, zinc borohydride or lithium borohydride is used, high specificity tends to be achieved. When the catalytic hydrogenation is employed, a catalyst which is used in the reduction of a ketone to an alcohol such as Pd/C, Pt/C, PtO$_2$ and the Raney nickel catalyst is used.

According to the present invention, the 3,5,6-trihydroxyhexanoic acid derivative (I) can be further treated to prepare a 3,5,6-trihydroxyhexanoic acid derivative of the formula:

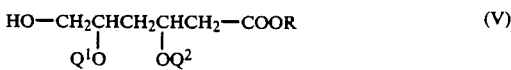

(V)

wherein $Q^1$ and $Q^2$ are hydroxyl-protecting groups or they may together form a ring, and R is an alkyl group, in which two secondary hydroxyl groups are protected.

To prepare the derivative (V), all the hydroxyl groups at the 3-, 5- and 6-positions are protected to prepare a protected 3,5,6-trihydroxyhexanoic acid derivative of the formula:

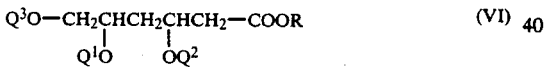

(VI)

wherein $Q^3$ is a hydroxyl-protecting group which can be selectively deprotected, and $Q^1$, $Q^2$ and R are the same as defined above.

In this step, the protecting groups are so selected that only the protecting group at the 6-position is deprotected while the protecting groups at the 3- and 5-positions and the ester group remain unchanged. When $Q^3$ is a benzoyl group, a substituted benzoyl group or a tert.-butyldimethylsillyl group, $Q^1$ and $Q^2$ are advantageously ketal type protecting groups such as acetonide groups and cyclohexylideneketal groups. Acetonidation may be effected with dimethoxypropane and/or acetone in an acidic condition according to a conventional method.

The 3,5,6-trihydroxyhexanoic acid derivative (VI) in which all the hydroxyl groups are protected is treated in an appropriate manner depending on the combination of the 6-position protecting group and the 3-and 5-position protecting groups to selectively deprotect the primary hydroxyl-protecing groups at the 6-position to obtain the compound (V). For example, when $Q^3$ is the benzoyl group, $Q^1$ and $Q^2$ are both acetonide groups and R is a tert.-butyl group, the compound (VI) is treated with sodium hydroxide in a mixture of water and methanol, whereby the hydroxyl-protecting group at the 6-position is easily deprotected. When $Q^3$ is the tert.-butyldimethylsillyl group, $Q^1$ and $Q^2$ are both acetonide groups and R is a tert.-butyl group, the compound (VI) is treated with tetrabutylammonium fluoride in tetrahydrofuran, whereby the hydroxyl-protecting group at the 6-position is easily deprotected.

Among the derivation (VI), a compound of the formula:

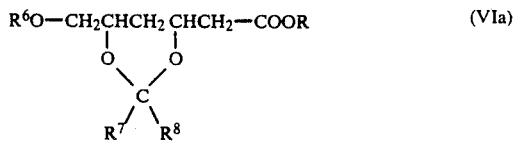

(VIa)

wherein $R^6$ is a triphenylmethyl group, a benzoyl group which may be substituted or a tert.-butyldimethylsilye group, $R^7$ and $R^8$ are independently hydrogen atoms, alkyl groups or aryl groups or form a cyclopentyl group or a cyclohexyl group together with the carbon atom to which they are bonded, and R is an alkyl group is a novel compound and in the scope of the present invention.

The preferred combinations of R, $R^6$, $R^7$ and $R^8$ are as follows:

$R^6$ is a benzoyl group, $R^7$ and $R^8$ are methyl groups and R is a tert.-butyl group, $R^6$ is a benzoyl group, one of $R^7$ and $R^8$ is a hydrogen atom and the other is a isopropyl group, and R is a tert.-butyl group, $R^6$ is a benzoyl group, one of $R^7$ and $R^8$ is a hydrogen atom and the other is a cyclohexyl group, and R is a tert.-butyl group, $R^6$ is a benzoyl group, one of $R^7$ and $R^8$ is a hydrogen atom and the other is a methyl group, and R is a tert.-butyl group, $R^6$ is a benzoyl group, one of $R^7$ and $R^8$ is a hydrogen atom and the other is a phenyl group, and R is a tert.-butyl group, $R^6$ is a benzoyl group, one of $R^7$ and $R^8$ is a methyl group and the other is an ethyl group, and R is a tert.-butyl group, and $R^6$ is a benzoyl group, $R^7$ and $R^8$ together form a cyclohexyl ring, and R is a tert.-butyl group.

PREFERRED EMBODIMENTS OF THE INVENTION

The present invention will be illustrated by following Examples, which will not limit the scope of the present invention.

EXAMPLE 1

S-3-Hydroxy-4-triphenylmethoxybutyronitrile

To a solution of S-3,4-dihydroxybutyronitrile (80.1 g) in pyridine (1 liter), a solution of trityl chloride (296.4 g) in methylene chloride (800 ml) was added at 0° C. and stirred at room temperature for 15 hours. After evaporating off volatile materials from the reaction solution under reduced pressure, methylene chloride (1 liter) and water (500 ml) were added and pH of the solution was adjusted to 7 with 6N hydrochloric acid. The solution was extracted with methylene chloride (1 liter×2), and the extract was dried over sodium sulfate followed by evaporation of the solvent under reduced pressure to obtain an oily product. To the oily product, a mixed solvent of ethyl acetate and hexane (1:5) was added to precipitate a crude product (205 g), which was recrystallized from the mixed solvent of ethyl acetate and hexane to obtain crystalline S-3-hydroxy-4-triphenylmethoxybutyronitrile (156.4 g). M.P. 147.5°-148.0° C.

¹H-NMR (CDCl₃): δ=2.57-2.67 (m, 1H), 2.53 (d, 2H, J=4 Hz), 3.25 (d, 2H, J=4 Hz), 3.80-4.13 (m, 1H), 7.22-7.62 (m, 15H).

IR (neat): 3400, 2280, 1500, 1460, 1230, 1120, 720 cm⁻¹.

$[\alpha]_D^{20} = -24.3$ (c=1, methanol).

EXAMPLE 2

S-3,4-O-Isopropylidene-3,4-dihydroxybutyronitrile

To a solution of S-3,4-dihydroxybutyronitrile (3.74 g,. 37 mmol) and 2,2-dimethoxypropane (16.4 g) in methylene chloride (50 ml), p-toluenesulfonic acid (0.12 g) was added and stirred at room temperature for 15 hours, and then a saturated aqueous solution of sodium hydrogencarbonate (50 ml) was added and stirred for 10 minutes. The resulting solution was extracted with methylene chloride (100 ml×b 3), and the extract was washed with saturated brine (100 ml×2). The organic layer was dried over sodium sulfate followed by evaporating off the solvent to obtain oily S-3,4-dihydroxybutyronitrile acetonide (4.3 g).

¹H-NMR (CDCl₃): δ=1.37 and 1.47 (2s, 6H), 2.63 (d, 2H, J=4 Hz), 3.66-4.50 (m, 3H).

IR (neat): 3000, 2250, 1390, 1380, 1160, 1080, 840, 520 cm⁻¹.

EXAMPLE 3

3S-Hydroxy-4-benzoyloxybutyronitrile

To a solution of S-3,4-dihydroxybutyronitrile (20 g) in pyridine (100 ml), benzoyl chloride (23.1 g) was added at 0° C. and stirred at room temperature for 4 hours and then water (300 ml) was added. After adjusting pH of the solution to 2 with 6N hydrochloric acid, the solution was extracted with methylene chloride (500 ml×2), and the extract was dried over sodium sulfate followed by evaporating off the solvent to obtain an oily product, which was purified with a silica gel column (hexane: acetone=2:1) to obtain 3S-hydroxy-4-benzoyloxybutyronitrile (27 g).

¹H-NMR (CDCl₃): δ=2.70 (d, 2H, J=6 Hz), 3.58-4.0 (m, 1H), 4.20-4.62 (m, 3H), 7.23-7.82 (m, 3H), 7.9-8.24 (m, 2H).

IR (neat): 3475, 2260, 1730, 1615, 1460, 1280, 1130, 720 cm⁻¹.

EXAMPLE 4

Ethyl 5S-hydroxy-6-triphenylmethoxy-3-oxohexanoate

To a mixture of active zinc powder (65.4 g) and anhydrous tetrahydrofuran (THF) (600 ml), ethyl bromoacetate (1.9 ml) was dropwise added at 70° C. and stirred at the same temperature for 20 minutes. To the resulting mixture, S-3-hydroxy-4-triphenylmethoxybutyronitrile (68.6 g) was added and then ethyl bromoacetate (88.9 ml) was dropwise added over 2 hours. The reaction mixture was stirred at 70° C. for one hour and cooled to 0° C. After adjusting pH of the solution to 2 with 6N hydrochloric acid, the solution was stirred at room temperature for 30 minutes. After adjusting pH to 7 with sodium hydrogencarbonate, the solid was filtered off, and the filtrate was extracted with ethyl acetate (500 ml×4). The organic layer was dried over sodium sulfate and the solvent was evaporated off to obtain an oily product, which was purified with a silica gel column (hexane:acetone=6:1) to obtain ethyl 5S-hydroxy-6-triphenyl-methoxy-3-oxohexanoate (60.6 g).

¹H-NMR (CDCl₃): δ=1.23 (t, 3H, J=7 Hz), 2.7 (d, 2H, J=6 Hz), 2.73-3.0 (m, 1H), 3.13 (d, 2H, J=6 Hz), 3.42 (s, 1H), 4.0-4.45 (m, 3H), 7.07-7.56 (m, 15H).

IR (soln): 3070, 3000, 1740, 1430, 1270, 905, 740 cm⁻¹.

EXAMPLE 5

Ethyl 5S-hydroxy-6-triphenylmethoxy- 3-oxohexanoate

To a mixture of active zinc powder (1.55 g) and anhydrous THF (12 ml), ethyl bromoacetate (0.2 ml) was dropwise added at 70° C. and stirred at the same temperature for 20 minutes. To the resulting mixture, S-3-hydroxy-4-triphenylmethoxybutyronitrile (1.37 g) was added and then ethyl bromoacetate (1.33 ml) was dropwise added over one hour. The reaction mixture was stirred at 70° C. for 20 minutes and cooled to room temperature. Then, to the mixture, THF (36 ml) and a 50% aqueous solution of potassium carbonate (3 ml) were added and stirred at room temperature for 30 minutes. After adding water (50 ml) and extracting with ethyl acetate (100 ml×3), the solvent was evaporated off to obtain an oily material. To the oily material, acetonitrile (10 ml), water (10 ml) and 1N hydrochloric acid (4 ml) were added and stirred at room temperature for 30 minutes. After evaporating off acetonitrile and extracting with ethyl acetate (100 ml×3), the extract was dried over sodium sulfate followed by evaporating off the solvent to obtain an oily product, which was purified with a silica gel column (hexane:acetone =6:1) to obtain ethyl 5S-hydroxy-6-triphenylmethoxy-3-oxohexanoate (953 mg).

EXAMPLE 6 tert.-Butyl 5S-hydroxy-6-triphenylmethoxy-3-oxohexanoate

To a mixture of active zinc powder (1.96 g) and anhydrous THF (30 ml), S-3-hydroxy-4-triphenylmethoxybutyronitrile (3.43 g) was added and then tert.-butyl bromoacetate (5.08 ml) was dropwise added at 70° C. over one hour. After stirring at 70° C. for further 20 minutes, the mixture was cooled to 5° C. and pH was adjusted to 1.8 with 6N hydrochloric acid followed by stirring for one hour. To the mixture, a saturated aqueous solution of sodium hydrogencarbonate was added to adjust pH to 7. The precipitated solid was filtered off and the filtrate was extracted with methylene chloride (100 ml ×2), and the extract was dried over sodium sulfate followed by evaporating off the solvent to obtain an oily product, which was purified with a silica gel column (hexane:acetone =5:1) to obtain tert. -butyl 5S-hydroxy-6-triphenylmethoxy-3-oxohexanoate (2.9 g).

¹H-NMR (CDCl₃): δ=1.43 (s, 9H), 2.73 (d, 2H, J=5 Hz), 3.33 (s, 2H), 4.0-4.3 (m, 1H), 7.17-7.53 (m, 15H).

IR (neat): 3600, 2970, 1710, 1140, 700 cm⁻¹.

$[\alpha]_D^{20} = -14.0$ (c=1.0, ethanol).

EXAMPLE 7 tert.-Butyl 5S-hydroxy-6-benzoyloxy-3-oxohexanoate

To a mixture of active zinc powder (1.96 g, 30 mmol) and anhydrous THF (30 ml), S-3-hydroxy-4-benzoyloxybutyronitrile (2.05 g) was added and then tert.-butyl bromoacetate (5.08 ml) was dropwise added at 70° C. over one hour. After stirring at 70° C. for further 20 minutes, the mixture was cooled to 5° C. and pH was adjusted to 1.8 with 6N hydrochloric acid followed by stirring for one hour. To the mixture, a saturated aqueous solution of sodium hydrogencarbonate was added to adjust pH to 7. The precipitated solid was filtered off and the filtrate was extracted with methylene chloride (100 ml×2), and the extract was dried over sodium sulfate followed by evaporating off the solvent to obtain an oily product, which was purified with a silica gel column (hexane:acetone=5:1) to obtain tert. -butyl 5S-hydroxy-6-benzoyloxy-3-oxohexanoate (355 mg).

$^1$H-NMR (CDCl$_3$): δ=1.46 (s, 9H), 2.85 (d, 2H, J=6 Hz), 3.09 (d, 1H, J=4 Hz), 3.42 (s, 2H), 4.32–4.6 (m, 3H), 7.26–7.6 (m, 3H), 8.0–8.11 (m, 2H).

IR (KBr): 3495, 1730, 1700, 1335, 1290, 1150, 720 cm$^{-1}$.

M.P.: 67°–68° C.

EXAMPLE 8

Ethyl S-5,6-O-isoprypylidene-5,6-dihydroxy-3-oxohexanoate

To a mixture of active zinc powder (13.9 g, 21.2 mmol) and anhydrous THF (100 ml), S-3,4-O-isopropylidene -3,4-dihydroxybutyronitrile (10 g) was added and then ethyl bromoacetate (23.6 ml) was dropwise added at 60° C. over one hour. After stirring at 60° C. for further one hour, the mixture was cooled to 5° C. and pH was adjusted to 2.5 with 6N hydrochloric acid followed by stirring for 30 minutes. To the mixture, 5N sodium hydroxide was added to adjust pH to 7. After adding sodium hydrogencarbonate (10 g), the precipitated solid was filtered off and the filtrate was extracted with ethyl acetate (150 ml×2), and the extract was dried over sodium sulfate followed by evaporating off the solvent to obtain an oily product, which was purified with a silica gel column (hexane:acetone=4:1) to obtain ethyl S-5,6-O-isoprypylidene-5,6-dihydroxy-3-oxohexanoate (12.4 g).

$^1$H-NMR (CDCl$_3$): δ=3.28 (t, 3H, J=6 Hz), 1.35 and 1.42 (2s, 6H), 2.75–2.98 (m, 2H), 3.48 (s, 2H), 3.45–3.68 (m, 1H), 4.15 (q, 2H), 4.0–4.6 (m, 2H).

IR (neat): 2990, 1740, 1720, 1240, 1070 cm$^{-1}$.

$[α]_D^{20}$=5.21 (c=1.2, ethanol).

EXAMPLE 9 tert.-Butyl S-5,6-O-isoprypylidene-5,6-dihydroxy-3-oxohexanoate

To a mixture of active zinc powder (3.92 g) and anhydrous THF (60 ml), S-3,4-O-isoprypylidene-3,4-dihydroxybutyronitrile (2.82 g) was added and then tert.-butyl bromoacetate (9.69 ml) was dropwise added at 70° C. over one hour. After stirring at 70° C. for further 20 minutes, the mixture was cooled to 5° C. and pH was adjusted to 2.5 with 6N hydrochloric acid followed by stirring for one hour. To the mixture, a saturated aqueous solution of sodium hydrogencarbonate was added to adjust pH to 7. The precipitated solid was filtered off and the filtrate was extracted with methylene chloride (200 ml×2), and the extract was dried over sodium sulfate followed by evaporating off the solvent to obtain an oily product, which was purified with a silica gel column (hexane:ethyl acetate=9:1) to obtain tert.-butyl S-5,6-O-isoprypylidene-5,6-dihydroxy-3-oxohexanoate (3.6 g).

$^1$H-NMR (CDCl$_3$): δ=1.37 and 1.43 (2s, 6H), 1.50 (s, 9H), 2.73–3.0 (m, 2H), 3.35 (s, 2H), 3.45–3.7 (m, 1H), 4.07–4.63 (m, 2H).

IR (neat): 2990, 1740, 1720, 1370, 1170 cm$^{-1}$.

$[α]_D^{20}$=6.59 (c=1.14, ethanol).

EXAMPLE 10

Ethyl 3,5-dihydroxy-6-triphenylmethoxyhexanoate

To a mixture of anhydrous THF (8 ml) and anhydrous ethanol (2 ml), sodium borohydride (57 mg) was added at −70° C. and stirred at the same temperature for 2 hours. After adding a saturated solution of sodium hydrogencarbonate (20 ml), the mixture was stirred at room temperature for 30 minutes. After extracting with methylene chloride (100 ml×3), the extract was dried over sodium sulfate and the solvent was evaporated off to obtain an oily product, which was purified with a silica gel column (hexane:acetone=3:1) to obtain ethyl 3,5-dihydroxy-6-triphenylmethoxyhexanoate (415 mg). HPLC analysis revealed that the product contained the (3R, 5S) isomer and the (3S, 5S) isomer in a molar ratio of 66:37. HPLC was carried out under following conditions:

Column: Fine pak SIL C$_{18-5}$ (Nippon Bunko Co., Ltd.) 4.6 mm ID×250 mm.

Column temperature: 40° C.

Developer: water/acetonitrile=65/35 (v/v).

Flow rate: 1.5 ml/min.

Detection: at 210 nm.

EXAMPLE 11

Ethyl (3R, 5S)-dihydroxy-6-triphenylmethoxy-hexanoate

To a mixture of anhydrous THF (336 ml) and anhydrous methanol (84 ml), a 1M solution of triethylboran in THF (46.2 mg) was added at room temperature and stirred at the same temperature for one hour. Then, a solution of ethyl 5S-hydroxy-6-triphenylmethoxy-3-oxohexanonate (13.3 g) in THF (30 ml) was added and stirred at −70° C. for 30 minutes. After adding sodium borohydride (1.49 g) and stirring at −70° C. for 2 hours, a saturated aqueous solution of ammonium chloride (200 ml) was gradually added while cooling and then a mixture of the saturated aqueous solution of ammonium chloride (200 ml), ethanol (100 ml) and a 30% hydrogen peroxide solution (100 ml) was gradually added. The mixture was stirred at room temperature for 30 minutes. After evaporating off THF under reduced pressure, the mixture was extracted with methylene chloride (500 ml×3), and the extract was dried over sodium sulfate followed by evaporating off the solvent to obtain an oily product, which was purified with a silica gel column (hexane:acetone=3:1) to obtain 3,5-dihydroxy-6-triphenylmethoxyhexanoic acid. HPLC revealed that the product contained the (3R, 5S) isomer favorably in a molar ratio of 95:5.

EXAMPLE 12 tert.-Butyl (3R, 5S)-dihydroxy-6-benzoyloxyhexanoate

To a mixture of anhydrous THF (17.1 ml) and anhydrous methanol (8.6 ml), a 1M solution of triethylboran in THF (9.35 mg) was added at room temperature and stirred at the same temperature for one hour. Then, a solution of tert.-butyl 5S-hydroxy-6-benzoyloxy-3-oxohexanoate (2.376 g) was added at −80° C. and stirred at the same temperature for 40 minutes. After adding sodium borohydride (364 mg) and stirring at −80° C. for 2 hours, a saturated aqueous solution of ammonium chloride (25 ml) was added while raising the temperature to 0° C. slowly. After stirring for 30 minutes, a mixture of a 30% hydrogen peroxide solution (12.5 ml) and ethanol (12.5 ml) was added. The mixture was stirred for further 30 minutes. After evaporating off THF and ethanol, the mixture was extracted with methylene chloride (100 ml×2), and the extract was dried over sodium sulfate followed by evaporating off the solvent to obtain an oily product, which was purified with a silica gel column (hexane:acetone=5:1) to obtain tert.-butyl 3,5-dihydroxy-6-benzoyloxyhexanoate. HPLC revealed that the product contained the (3R, 5S) isomer favorably in a molar ration of 98:2.

$^1$H-NMR (CDCl$_3$): δ=1.47 (s, 9H), 1.63-1.82 (m, 2H), 2.45 (d, 2H, J=5 Hz), 4.1-4.3 (m, 4H), 7.32-7.7 (m, 3H), 8.0-8.22 (m, 2H).

IR (neat): 3450, 3000, 1730, 1040, 850, 720 cm$^{-1}$.

EXAMPLE 13 tert.-butyl (3R, 5S)-dihydroxy-6-benzoyloxyhexanoate

To a solution of tert.-butyl 5S-hydroxy-6-benzoyloxy-3-oxohexanoate (200 mg) in anhydrous THF (2 ml), a 1M solution of diisobutylaluminum hydride in hexane (24 ml) was added at −75° C. and stirred at the same temperature for 4.5 hours. While raising the temperature to 0° C. slowly, pH of the mixture was adjusted to 7 with 1N hydrochloric acid. Then, the mixture was extracted with ethyl acetate (10 ml×2), and the extract was dried over sodium sulfate followed by evaporating off the solvent to obtain an oily product, which was purified with a silica gel column (hexane:acetone=5:1) to obtain tert.-butyl 3,5-dihydroxy-6-benzoyloxyhexanoate (190 mg). HPLC revealed that the product contained the (3R, 5S) isomer favorably in a molar ratio of 80:20.

EXAMPLE 14

Ethyl (3R, 5S)-5,6-O-isopropylidene-3,5,6-trihydroxyhexanoate

To a 1M solution of lithium borohydride in THF (29 ml), a solution of S-5;6-isopropylidene-5,6-dihydroxy-3-oxohexanoate (3.34 g) in anhydrous THF (4.3 ml) was dropwise added over one hour and stirred at −70° C. for 2 hours. While raising the temperature from −70° to 0° C., 2N hydrochloric acid (12 ml) was added to adjust pH to 7. After evaporating off THF, the mixture was extracted with ethyl acetate (50 ml×2). The extract was dried over sodium sulfate followed by evaporating off the solvent to obtain an oily product, which was purified with a silica gel column (hexane:acetone=5:1) to obtain ethyl 5,6-O-isopropylidene-3,5,6-trihydroxyhexanoate (2.9 g). HPLC revealed that the product contained the (3R, 5S) isomer favorably in a molar ratio of 78:22. HPLC was carried out under following conditions:

Column: Chiral Cell OJ (Daicel Co., Ltd.) 4.6 mm ID×250 mm.
Column temperature: 25° C.
Developer: hexane/isopropanol=92/8 (v/v).
Flow rate: 0.9 ml/min.
Detection: at 210 nm.

$^1$H-NMR (CDCl$_3$): δ=1.27 (t, 3H, J=6 Hz), 1.35 and 1.4 (2s, 6H), 1.63-1.93 (m, 2H), 2.50 (d, 2H, J=6 Hz), 3.2-3.74 (m, 2H), 4.01-4.53 (m, 5H).

IR (neat): 3470, 3000, 1730, 1380, 1180, 1160 cm$^{-1}$.

EXAMPLE 15 tert.-Butyl (3R, 5S)-6-benzoyloxy-3,5-O-isopropylidene-3,5-dihydroxyhexanoate

To a solution of tert.-butyl (3R, 5S)-dihydroxy-6-benzoyloxyhexanoate (8.94 g) in methylene chloride (22.5 ml), 2,2-dimethoxypropane (35.8 ml) and p-toluenesulfonic acid (269 mg) were added and stirred at room temperature for 4 hours and then a saturated aqueous solution of sodium hydrogencarbonate (500 ml) was added. After separating the aqueous layer and the organic layer, the aqueous layer was extracted with methylene chloride (20 ml×2). The combined organic layer was dried over sodium sulfate and the solvent was evaporated off to obtain an oily product, which was purified with a silica gel column (hexane:acetone=10:1) to obtain crystalline tert.-butyl (3R, 5S)-6-benzoyloxy-3,5-O-isopropylidene-3,5-dihydroxyhexanoate (7.24 g).

$^1$H-NMR (CDCl$_3$): δ=1.44 (s, 9H), 1.45 (d, 6H, J=3 Hz), 1.55-1.59 (m, 2H), 2.35-2.46 (m, 2H), 4.22-4.37 (m, 4H), 7.43-7.59 (m, 3H), 8.0-8.1 (m, 2H).

IR (neat): 2975, 1720, 1270, 1150, 1100, 718 cm$^{-1}$.
M.P. 55°-56° C.

EXAMPLE 16 tert.-Butyl (3R, 5S)-6-benzoyloxy-3,5-O-isobutylidene-3,5-dihydroxyhexanoate

To a solution of tert.-butyl (3R, 5S)-dihydroxy-6-benzoyloxyhexanoate (1 g) in methylene chloride (5 ml), isobutylaldehyde (1 ml) and p-toluenesulfonic acid (10 mg) were added and stirred at room temperature for 3 hours and then a saturated aqueous solution of sodium hydrogencarbonate (2 ml) was added. After separating the aqueous layer and the organic layer, the aqueous layer was extracted with methylene chloride (50 ml×2). The combined organic layer was dried over sodium sulfate followed by evaporating off the solvent to obtain an oily product, which was purified with a silica gel column (hexane:acetone=10:1) to obtain oily tert.-butyl (3R, 5S)-6-benzoyloxy-3,5-O-isobutylidene-3,5-dihydroxyhexanoate (808 mg).

$^1$H-NMR (CDCl$_3$): δ=0.93 (d, 6H, J=6 Hz), 1.45 (s, 9H), 1.57-2.03 (m, 3H), 2.4-2.6 (m, 2H), 3.9-4.27 (m, 2H), 4.27-4.93 (m, 1H), 7.26-7.73 (m, 3H), 7.98-8.2 (m, 2H).

IR (neat): 3000, 1725, 1400, 1310, 1060, 750 cm$^{-1}$.

EXAMPLE 17 tert.-Butyl (3R, 5S)-6-benzoyloxy-3,5-O-cyclohexylmethylene-3,5-dihydroxyhexanoate In the same manner as in Example 16 but using cyclohexanecarboxyaldehyde (521 mg) in place of isobutylaldehyde, the reaction and purification were carried out to obtain oily tert.-butyl (3R, 5S)-6-benzoyloxy-3,5-O-cyclohexylmethylene-3,5-dihydroxyhexanoate (811 mg).

$^1$H-NMR (CDCl$_3$): δ=0.93-2.0 (m, 13H), 1.4 (s, 9H), 2.37-2.58 (m, 2H), 3.80-4.17 (m, 2H), 4.17-4.4 (m, 3H), 7.28-7.65 (m, 3H), 7.92-8.1 (m, 3H).

IR (neat): 2950, 1760, 1490, 1410, 1320, 1070, 760 cm$^{-1}$.

EXAMPLE 18 tert.-Butyl (3R, 5S)-6-benzoyloxy-3,5-O-ethylidene-3,5-dihydroxyhexanoate

In the same manner as in Example 16 but using acetaldehyde (1 ml) in place of isobutylaldehyde, the reaction and purification were carried out to obtain oily tert.-butyl (3R, 5S)-6-benzoyloxy-3,5-O-ethylidene-3,5-dihydroxyhexanoate (733 mg).

$^1$H-NMR (CDCl$_3$): δ=0.33 (d, 3H, J=4 Hz), 1.43 (s, 9H), 1.56–1.87 (m, 2H), 2.46 (t, 2H, J=6 Hz), 3.9–4.25 (m, 2H), 4.36 (d, 2H, J=4 Hz), 4.77 (q, 1H, J=4 Hz), 7.37–7.66 (m, 3H), 8.03–8.23 (m, 2H).

IR (neat): 3000, 1720, 1370, 960, 850, 720 cm$^{-1}$.

EXAMPLE 19 tert.-Butyl (3R, 5S)-6-benzoyloxy-3,5-O-(1-methylpropylidene)-3,5-dihydroxyhexanoate To an ice-cooled solution of p-toluenesulfonic acid monohydrate (111 mg, 0.58 mmol) and methyl orthoformate (0.58 ml, 5.3 mmol) in methylene chloride (9 ml), methyl ethyl ketone (3.6 ml, 40 mmol) was dropwise added over 5 minutes. After 10 minutes, the temperature was raised to room temperature, and the mixture was stirred for 2 hours and then added to a solution of tert.-butyl (3R, 5S)-6-benzoyloxy-3,5-dihydroxyhexanoate (109 g, 3.4 mmol) in methylene chloride (0.5 ml). After one hour and two hours, methyl orthoformate (each 0.58 ml) was added, and after three hours, a 5% aqueous solution of sodium hydrogencarbonate (5 ml) was added. After stirring, the mixture was extracted with methylene chloride (30 ml×2). The extract was dried over sodium sulfate, filtered and concentrated under reduced pressure to obtain a brown oily product (1.15 g), which was purified with a silica gel column (hexane:acetone=100:1) to obtain colorless oily tert.-butyl (3R, 5S)-6-benzoyloxy-3,5-O-(1-methylpropylidene)-3,5-dihydroxyhexanoate (0.72 g, 1.9 mmol, 57%).

$^1$H-NMR (CDCl$_3$): δ=0.91 (3H, t, J=6 Hz), 1.43 (9H, s), 1.3–2.1 (7H, m), 2.2–2.7 (2H, m), 4.1–4.5 (4H, m), 7.3–7.7 (3H, m), 8.0–8.2 (2H, m).

IR (neat): 2980, 1720, 1610, 1460, 1380, 1290, 1170, 970, 860, 730 cm$^{-1}$.

$[α]_D^{20}$= +1.33° (c=1.052, methanol).

EXAMPLE 20 tert.-Butyl (3R, 5S)-6-benzoyloxy-3,5-O-(1,3-dimethylbutylidene)-3,5-dihydroxyhexanoate In the same manner as in Example 19 but using methyl isobutyl ketone in place of methyl ethyl ketone, the reaction was carried out to obtain colorless oily tert.-butyl (3R, 5S)-6-benzoyloxy-3,5-O-(1,3-dimethylbutylidene)-3,5-dihydroxyhexanoate. Yield, 40%.

$^1$H-NMR (CDCl$_3$): δ=0.92 (6H, d, J=6 Hz), 1.43 (9H, s), 1.2–2.1 (8H, m), 2.1–2.6 (2H, m), 4.0–4.5 (4H, m), 7.3–7.6 (3H, m), 7.9–8.2 (2H, m).

IR (neat): 2975, 1730, 1615, 1460, 1380, 1295, 1165, 965, 860, 730 cm$^{-1}$.

$[α]_D^{20}$= −0.70° (c=1.136, methanol).

EXAMPLE 21 tert.-Butyl (3R, 5S)-6-benzoyloxy-3,5-O-cyclohexylidene)-3,5-dihydroxyhexanoate To a solution of tert.-butyl (3R, 5S)-6-benzoyl-oxy-3,5-dihydroxyhexanoate (608 mg, 1.87 mmol) and 1,1-dimethoxycyclohexane (0.58 ml, 3.79 mmol) in methylene chloride (3 ml), p-toluenesulfonic acid monohydrate (18 mg, 0.09 mmol) was added and stirred at room temperature for 17 hours. Then, additional 1,1-dimethoxycyclohexane (0.29 ml, 1,89 mmol) was added and reacted for 2 hours. After adding a 5% aqueous solution of sodium hydrogencarbonate (5 ml), the stirring was continued for 5 minutes. The mixture was extracted with methylene chloride (20 ml×2). The extract was dried over anhydrous sodium sulfate, filtered and concentrated under reduced pressure to obtain a brown oily product, which was purified with a silica gel column (hexane:acetone=100:1.5) to obtain colorless oily product (partially solidified) (390 mg). The colorless oily product was crystallized from hexane to obtain tert.-butyl (3R, 5S)-6-benzoyloxy-3,5-O-cyclohexylidene-3,5-dihydroxyhexanoate (290 mg, 0.72 mmol, 38%).

$^1$H-NMR (CDCl$_3$): δ=1.43 (9H, s), 1.2–2.1 (12H, m), 2.2–2.6 (2H, m), 4.1–4.5 (4H, m), 7.3–7.6 (3H, m), 7.9–8.2 (2H, m).

IR (KBr): 2950, 1720, 1280, 1260, 1155, 1120, 985, 735 cm$^{-1}$.

$[α]_D^{20}$= −0.79° (c=1.004, methanol).

M.P. 78°–80° C.

EXAMPLE 22 tert.-Butyl (3R, 5S)-3,5-O-isopropylidene-3,5,6-trihydroxyhexanoate

To a solution of tert.-butyl (3R, 5S)-6-benzoyloxy-3,5-O-isopropylidene-3,5-dihydroxyhexanoate (3.64 g) in methanol (36 ml), 1N sodium hydroxide (10 ml) was added and stirred at room temperature for 2 hours. To the resulting solution, 1H hydrochloric acid was gradually added while cooling on ice to adjust pH to 7. After evaporating off methanol under reduced pressure, the residual aqueous solution was extracted with methylene chloride (70 ml×2), and the extract was dried over sodium sulfate followed by evaporating off the solvent to obtain an oily product, which was purified with a silica gel column (hexane:acetone=5:1) to obtain oily tert.-butyl (3R, 5S)-3,5-O -isopropylidene-3,5,6-trihydroxyhexanoate (2,34 g).

$^1$H-NMR (CDCl$_3$): δ=1.45 (d, 6H, J=4 Hz), 1.47 (s, 9H), 1.5–1.82 (m, 2H), 2.32–2.71 (m, 3H), 3.44–3.68 (m, 2H), 3.82–4.43 (m, 2H).

IR (neat): 2980, 1720, 1363, 1200, 1150, 1020 cm$^{-1}$.

$[α]_D^{20}$= −5.90° (c=2.0, methanol).

EXAMPLE 23 tert.-Butyl (3R, 5S)-3,5-O-isobutylidene-3,5,6-trihydroxyhexanoate

To a solution of tert.-butyl (3R, 5S)-6-benzoyloxy-3,5-O-isobutylidene-3,5-dihydroxyhexanoate (500 mg) in methanol (5 ml), 1N sodium hydroxide (1.38 ml) was added at room temperature over 5 minutes and stirred at the same temperature for 2.5 hours. After adding water (10 ml), the mixture was neutralized to pH of 7 with 1N hydrochloric acid and extracted with methylene chloride (25 ml×2). The extract was dried over anhydrous sodium sulfate followed by evaporating off the solvent to obtain a colorless oily product (362 mg), which was purified with a silica gel column (hexane:acetone=10:1) to obtain colorless oily tert.-butyl (3R, 5S)-3,5-O-isobutylidene-3,5,6-trihydroxyhexanoate (292 mg).

$^1$H-NMR (CDCl$_3$): δ=0.933 (d, 6H, J =5 Hz), 1.42 (s, 9H), 1.56–2.36 (m, 3H), 2.34–2.58 (m, 2H), 3.46–4.23 (m, 4H), 4.3 (d, 2H, J=5 Hz).

IR (neat): 3500, 3000, 1740, 1495, 1040, 980, 860 cm$^{-1}$.

EXAMPLE 24 tert.-Butyl (3R, 5S)-3,5-O-cyclohexylmethylene-3,5,6-trihydroxyhexanoate

In the same manner as in Example 23, tert.-butyl (3R, 5S)-6-benzoyloxy-3,5-O-cyclohexylmethylene-3,5-dihydroxyhexanoate (500 mg) was treated with 1N sodium hydroxide (1.2 ml), worked up and purified to obtain colorless oily tert.-butyl (3R, 5S)-3,5-O -cyclohexylmethylene-3,5,6-trihydroxyhexanoate (313 mg).

$^1$H-NMR (CDCl$_3$): δ=0.87–2.22 (m, 1H), 2.33–2.52 (m, 2H), 3.48–4.16 (m, 4H), 4.25 (d, 1H, 4=6 Hz).

IR (neat): 3450, 2930, 1720, 1460, 1370, 1150, 1030, 850, 740 cm$^{-1}$.

EXAMPLE 25 tert.-Butyl (3R, 5S)-3,5-O-ethylidene-3,5,6-trihydroxyhexanoate

In the same manner as in Example 23, tert.-butyl (3R, 5S)-6-benzoyloxy-3,5-O-ethylidene-3,5-dihydroxyhexanoate (500 mg) was treated with 1N sodium hydroxide (1.5 ml), worked and purified with a silica gel column (hexane:acetone=10:1) to obtain colorless oily tert.-butyl (3R, 5S)-3,5-O-ethylidene-3,5,6-trihydroxyhexanoate (226 mg).

$^1$H-NMR (CDCl$_3$): δ=1.33 (d, 3H, J=6 Hz), 1.42 (s, 9H), 1.77–2.36 (m, 2H), 2.48 (t, 3H, J=6 Hz), 3.5–4.32 (m, 4H), 4.83 (q, 1H, J=6 Hz).

IR (neat): 3450, 3000, 1730, 1380, 1160, 1035, 960 cm$^{-1}$.

EXAMPLE 26 tert.-Butyl (3R, 5S)-3,5-O-(1-methylpropylidene)-3,5,6-trihydroxyhexanoate

To a solution of tert.-butyl (3R, 5S)-6-benzoyloxy-3,5-O-(1-methylpropylidene)-3,5-dihydroxyhexanoate prepared in Example 19 (0.42 g, 1.1 mmol) in methanol (4 ml), 1N sodium hydroxide (1.4 ml, 1.4 mmol) was added at room temperature over 5 minutes and stirred for 1 hours. After adding water (10 ml), the mixture was neutralized to pH of 7 with 1N hydrochloric acid and extracted with methylene chloride (25 ml×2). The extract was dried over anhydrous sodium sulfate, filtered and concentrated under reduced pressure to obtain a colorless oily product (0.40 g), which was purified with a silica gel column (hexane:acetone=100:4) to obtain colorless oily tert.-butyl (3R, 5S)-3,5-O-(1-methylpropylidene)-3,5,6-trihydroxyhexanoate (280 mg, 1.0 mmol, 92%).

$^1$H-NMR (CDCl$_3$): δ=0.92 (3H, t, J=7.5 Hz), 1.45 (9H, s), 1.2–1.9 (7H, m), 2.1 (1H, brs), 2.1–2.6 (2H, m), 3.4–3.7 (2H, m), 3.8–4.2 (1H, m), 4.1–4.5 (1H, m).

IR (neat): 3450, 2970, 1735, 1380, 1160, 955, 850 cm$^{-1}$.

$[α]_D^{20}$= −10.35° (c=1.024, methanol).

EXAMPLE 27 tert.-Butyl (3R, 5S)-3,5-O-(1,3-dimethylbutylidene)-3,5,6-trihydroxyhexanoate In the same manner as in Example 26 but using tert.-butyl (3R, 5S)-6-benzoyloxy-3,5-O-(1,3-dimethylbutylidene)-3,5-dihydroxyhexanoate prepared in Example 20 in place of tert.-butyl (3R, 5S)-6-benzoyloxy-3,5-O-(1-methylpropylidene)-3,5-dihydroxyhexanoate, the reaction was carried out to obtain colorless oily tert.-butyl (3R, 5S)-3,5-O-(1,3-dimethylbutylidene)-3,5,6-trihydroxyhexanoate. Yield, 81%.

$^1$H-NMR (CDCl$_3$): δ=0.93 (6H, d, J=6 Hz), 1.45 (9H, s), 1.2–2.0 (8H, m), 2.2–2.6 (3H, m), 3.4–3.7 (2H, m), 3.9–4.2 (1H, m), 4.1–4.5 (1H, m).

IR (neat): 3500, 2980, 1740, 1385, 1265, 1160, 965, 860 cm$^{-1}$.

$[α]_D^{20}$= −12.18° (c=1.034, methanol).

EXAMPLE 28 tert.-Butyl (3R, 5S)-3,5-O-cyclohexylidene-3,5,6-trihydroxyhexanoate

In the same manner as in Example 26 but using tert.-butyl (3R, 5S)-6-benzoyloxy-3,5-O-cyclohexylidene-3,5-dihydroxyhexanoate prepared in Example 21 in place of tert.-butyl (3R, 5S)-6-benzoyloxy-3,5-O-(1-methylpropylidene)-3,5-dihydroxyhexanoate, the reaction was carried out to obtain colorless oily tert.-butyl (3R, 5S)-3,5-O-cyclohexylidene-3,5,6-trihydroxyhexanoate. Yield, 85%.

$^1$H-NMR (CDCl$_3$): δ=1.47 (9H, s), 1.0–2.2 (12H, m), 1.27 (1H, brs), 2.1–2.6 (2H, m), 3.3–3.7 (2H, m), 3.9–4.3 (1H, m), 4.2–4.5 (1H, m).

IR (neat): 3470, 2960, 1740, 1380, 1170, 980 cm$^{-1}$.

$[α]_D^{20}$= −16.06° (c=1.046, methanol).

What is claimed is:

1. A process for the production of a 3,5,6-trihydroxyhexanoic acid derivative of the formula:

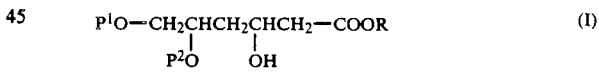

wherein P$^1$ and P$^2$ are independently hydrogen atoms or hydroxyl-protecting groups, or together form a ring, and R is an alkyl group, which comprises steps of:

reacting a butyronitrile derivative of the formula:

wherein P$^1$ and P$^2$ are the same as defined above with an α-haloacetate of the formula:

wherein X is a halogen atom, and R is the same as defined above in the presence of a metallic catalyst selected from the group consisting zinc and zinc-copper to form an intermediate product which is then hydrolyzed to a keto acid derivative of the formula:

$$P^1O-CH_2CHCH_2CCH_2-COOR \quad (IV)$$
$$\phantom{P^1O-CH_2C}|\phantom{HCH_2C}\|$$
$$\phantom{P^1O-CH_2CH}P^2O\phantom{CH_2C}O$$

wherein $P^1$, $P^2$ and R are the same as defined above, and then reducing the obtained keto acid derivative of the formula (IV).

2. The process of claim 1, wherein an optically active (3S)-butyronitrile derivative is used as the butyronitrile derivative of the formula (II), and an optically active (5S)-trihydroxyhexanoic acid derivative is obtained as the 3,5,6-trihydroxyhexanoic acid of the formula (I).

3. The process of claim 1, wherein a compound of the formula:

$$TrO-CH_2CHCH_2-CN \quad (IIa)$$
$$\phantom{TrO-CH_2C}|$$
$$\phantom{TrO-CH_2CH}OH$$

wherein Tr is a triphenylmethyl group is used as the butyronitrile derivative of the formula (II).

4. The process of claim 1, wherein a compound of the formula:

$$\begin{array}{c} O-CH_2CHCH_2-CN \\ | \quad\quad\quad | \\ R^1-C\quad\quad\quad O \\ | \\ R^2 \end{array} \quad (IIb)$$

wherein $R^1$ and $R^2$ are independently hydrogen atoms, alkyl groups or aryl groups, or together form a 5- or 6-membered ring together with the carbon atom to which they are bonded is used as the butyronitrile derivative of the formula (II).

5. The process of claim 1, wherein a compound of the formula:

$$\begin{array}{c} R^3 \\ | \\ R^4-SiO-CH_2CHCH_2-CN \\ | \quad\quad\quad\quad | \\ R^2 \quad\quad\quad\quad OH \end{array} \quad (IIC)$$

wherein $R^2$ is hydrogen, an alkyl or aryl group, $R^3$ and $R^4$ are independently alkyl or aryl groups, is used as the butyronitrile derivative of the formula (II).

6. The process of claim 1, wherein a compound of the formula:

$$R^5-\text{C}_6\text{H}_4-COO-CH_2CHCH_2-CN \quad (IId)$$
$$\phantom{R^5-C_6H_4-COO-CH_2C}|$$
$$\phantom{R^5-C_6H_4-COO-CH_2CH}OH$$

wherein $R^5$ is a hydrogen atom, an alkyl, alkoxy group or a halogen atom is used as the butyronitrile derivative of the formula (II).

7. The process of claim 1, wherein X in the α-haloacetate of the formula (III) is a bromine atom.

8. A process for the production of 3,5,6-trihydroxyhexanoic acid derivatives of the formula:

$$HO-CH_2CHCH_2CHCH_2-COOR \quad (V)$$
$$\phantom{HO-CH_2C}|\phantom{HCH_2C}|$$
$$\phantom{HO-CH_2CH}Q^1O\phantom{CH_2C}OQ^2$$

wherein $Q^1$ and $Q^2$ are hydroxyl-protecting groups which may together form a ring, and R is an alkyl group, wich comprises steps of:

reacting a butyronitrile derivative of the formula:

$$P^1O-CH_2CHCH_2-CN \quad (II)$$
$$\phantom{P^1O-CH_2C}|$$
$$\phantom{P^1O-CH_2CH}P^2O$$

wherein $p^1$ and $p^2$ are independently hydrogen atoms or hydroxyl-protecting groups which may together form a ring with an α-haloacetate of the formula:

$$X-CH_2-COOR \quad (III)$$

wherein X is a halogen atom, and R is the same as defined above, in the presence of a metallic catalyst selected from the group consisting of zinc and zinc-copper to form an intermediate product which is then hydrolyzed to a keto acid derivative of the formula:

$$P^1O-CH_2CHCH_2CCH_2-COOR \quad (IV)$$
$$\phantom{P^1O-CH_2C}|\phantom{HCH_2C}\|$$
$$\phantom{P^1O-CH_2CH}P^2O\phantom{CH_2C}O$$

wherein $p^1$, $p^2$ and R are the same as defined above, reducing the obtained keto acid derivative to form a 3,5,6-trihydroxyhexanoic acid derivative of the formula:

$$P^1O-CH_2CHCH_2CHCH_2-COOR \quad (I)$$
$$\phantom{P^1O-CH_2C}|\phantom{HCH_2C}|$$
$$\phantom{P^1O-CH_2CH}P^2O\phantom{CH_2C}OH$$

wherein $p^1$, $p^2$ and R are the same as defined above, protecting all of the hydroxy groups in the intermediate (I) to form a derivative of the formula:

$$Q^3O-CH_2CHCH_2CHCH_2-COOR \quad (VI)$$
$$\phantom{Q^3O-CH_2C}|\phantom{HCH_2C}|$$
$$\phantom{Q^3O-CH_2CH}Q^1O\phantom{CH_2C}OQ^2$$

wherein $Q^3$ is a hydroxyl-protecting group which can be selectively deprotected, and $Q^1$, $Q^2$ and R are the same as defined above, and then selectively deprotecting the group $Q^3$.

* * * * *